United States Patent
Sharkey et al.

(10) Patent No.: US 6,461,357 B1
(45) Date of Patent: Oct. 8, 2002

(54) ELECTRODE FOR ELECTROSURGICAL ABLATION OF TISSUE

(75) Inventors: Hugh R. Sharkey, Woodside; Gary S. Fanton, Portola Valley; John A. Ashley, San Francisco; J. Remberto Carranza, Daly City, all of CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/340,065

(22) Filed: Jun. 25, 1999

Related U.S. Application Data

(63) Continuation-in-part of application No. 09/022,612, filed on Feb. 12, 1998, now Pat. No. 6,135,999.
(60) Provisional application No. 60/037,782, filed on Feb. 12, 1997.

(51) Int. Cl.[7] .................................................. A61B 18/14
(52) U.S. Cl. ........................................... 606/45; 606/48
(58) Field of Search .............................. 606/41, 45, 46, 606/48–50

(56) References Cited

U.S. PATENT DOCUMENTS

| | | |
|---|---|---|
| 164,184 A | 8/1875 | Kidder |
| 300,155 A | 10/1884 | Starr |
| 371,664 A | 10/1887 | Brannan et al. |
| 452,220 A | 5/1891 | Gunning |
| 1,314,855 A | 9/1919 | Carpenter |
| 1,366,756 A | 1/1921 | Wappler |
| 1,731,627 A | 10/1929 | Johnson et al. |
| 1,735,271 A | 12/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 11/1934 | Kimble |
| 2,002,594 A | 5/1935 | Wappler et al. |
| 2,004,559 A | 6/1935 | Wappler et al. |
| 2,050,904 A | 8/1936 | Trice |
| 2,056,377 A | 10/1936 | Wappler |

(List continued on next page.)

FOREIGN PATENT DOCUMENTS

| | | | |
|---|---|---|---|
| DE | 39 18316 | 3/1990 | ............ A61B/17/39 |
| EP | 0 648 475 A | 4/1995 | |
| EP | 0 682 910 A1 | 11/1995 | ............. A61B/1/00 |
| EP | 0 737 487 A2 | 10/1996 | ........... A61M/25/01 |
| FR | 2 645 008 | 10/1990 | ........... A61B/17/32 |
| WO | WO 82/02488 | 8/1982 | ............ A61B/17/39 |
| WO | WO 92/05828 | 4/1992 | ........... A61M/25/00 |
| WO | WO 93/16648 | 9/1993 | ........... A61B/17/32 |
| WO | WO 95/10981 | 4/1995 | ............. A61B/8/12 |
| WO | WO 95/25471 | 9/1995 | ............ A61B/17/39 |
| WO | WO 96/11638 | 4/1996 | ........... A61B/17/32 |
| WO | WO 96/32885 | 10/1996 | ............. A61B/5/04 |
| WO | WO 96/34559 | 11/1996 | .......... A61B/5/0402 |
| WO | WO 98/17190 | 4/1998 | ........... A61B/18/00 |
| WO | WO 98 34558 A | 8/1998 | |

*Primary Examiner*—Lee Cohen
(74) *Attorney, Agent, or Firm*—Dorsey & Whitney LLP

(57) ABSTRACT

An electrosurgical probe is provided to vaporize, cut, coagulate or remove tissue from a body structure. A method of surgically treating a mammal includes providing a surgical instrument including a length of shaft and an active electrode having a curved current density edge with at least one convex surface; and ablating a tissue surface with said surgical instrument.

47 Claims, 16 Drawing Sheets

Ashtray Electrode Unipolar

U.S. PATENT DOCUMENTS

| Patent | Date | Inventor | Class |
|---|---|---|---|
| 2,224,464 A | 12/1940 | Wolf | |
| 2,275,167 A | 3/1942 | Bierman | |
| 2,888,928 A | 6/1959 | Seiger | |
| 3,152,590 A | 10/1964 | Zurdo et al. | |
| 3,163,165 A | 12/1964 | Isakawa | |
| 3,460,539 A | 8/1969 | Anhalt, Sr. | |
| 3,595,239 A | 7/1971 | Petersen | |
| 3,768,482 A | 10/1973 | Shaw | |
| 3,828,780 A | 8/1974 | Morrison, Jr. | |
| 3,870,047 A | 3/1975 | Gonser | |
| 3,901,242 A | 8/1975 | Storz | |
| 3,902,494 A | 9/1975 | Haberlin | |
| 3,920,021 A | 11/1975 | Hiltebrandt | |
| 3,920,022 A | 11/1975 | Pastor | |
| 3,938,527 A | 2/1976 | Rioux et al. | |
| 3,987,795 A | 10/1976 | Morrison | |
| 4,784,161 A | 11/1988 | Skalsky et al. | |
| 4,846,175 A | 7/1989 | Frimberger | 128/303.15 |
| 4,927,420 A | 5/1990 | Newkirk et al. | |
| 5,009,656 A | 4/1991 | Reimels | 606/48 |
| 5,114,402 A | 5/1992 | McCoy | 604/95 |
| 5,152,748 A | 10/1992 | Chastagner | 604/95 |
| 5,277,696 A | 1/1994 | Hagen | |
| 5,279,559 A | 1/1994 | Barr | 604/95 |
| 5,281,218 A | 1/1994 | Imran | |
| 5,364,395 A | 11/1994 | West, Jr. | |
| 5,415,633 A | 5/1995 | Lazarus et al. | 604/95 |
| 5,433,739 A | 7/1995 | Sluijter et al. | 607/99 |
| 5,458,596 A | 10/1995 | Lax et al. | |
| 5,514,130 A | 5/1996 | Baker | |
| 5,569,244 A * | 10/1996 | Hahnen | 606/46 |
| 5,643,255 A | 7/1997 | Organ | |
| 5,693,050 A * | 12/1997 | Speiser | 606/41 |
| 5,779,699 A * | 7/1998 | Lipson | 606/41 |
| 5,785,705 A | 7/1998 | Baker | 606/32 |
| 5,888,198 A | 3/1999 | Eggers et al. | |
| 6,093,185 A * | 7/2000 | Ellis et al. | 606/32 |
| 6,135,999 A | 10/2000 | Fanton et al. | |
| 6,179,836 B1 * | 1/2001 | Eggers et al. | 606/45 |
| 6,245,069 B1 * | 6/2001 | Gminder | 606/45 |

* cited by examiner

Medial (side) View

Ashtray

Ashtray

Dome

Dome

Dome with dimple

Dome with dimple

Ashtray Electrode Unipolar

Cross Fire
Unipolar, Electrode

ELECTRODE FOR ELECTROSURGICAL ABLATION OF TISSUE

CROSS REFERENCE TO RELATED APPLICATIONS

This application is a continuation-in-part under 35 U.S.C. 120 of U.S. Ser. No. 09/022,612, filed Feb. 12, 1998, now U.S. Pat. No. 6,135,989, which is a continuation-in-part of Ser. No. 60/037,782, filed Feb. 12, 1997 both of which are incorporated herein by reference in their entirety.

BACKGROUND OF THE INVENTION

The invention relates to surgical systems applying thermal energy to biological tissue to modify the characteristics of the tissue. More particularly, the invention is directed to electrosurgical probes utilizing radiofrequency (RF) energy to cut, coagulate, ablate and/or vaporize the tissue during a medical procedure for treatment and therapy.

Arthroscopic surgery is becoming increasingly popular, because it generally does less damage, is less invasive and is safer than open procedures and produces less scarring in and around joints. This type of surgery further results in a faster healing response and a quicker return of the patient to full productivity while reducing costs of open surgical procedures.

Nevertheless, arthroscopic surgery has its limitations. The surgeon must operate through a narrow tube, which is awkward. Only one probe can be used at a time. Often the viewing camera is positioned at an angle which is different from the surgeon's normal gaze. This contrasts with "open surgery" where the surgeon has relative ease of viewing the surgical site and can freely move both hands, even utilizing the hands of colleagues.

In view of such difficulties of arthroscopic surgery, it is understandable that laser, microwave and radiofrequency (RF) probes which simultaneously cut and coagulate are preferred. However, current probes are poorly adapted to certain activities, such as cutting narrow tendons or ligaments. Current probes have convex, pointed and/or flat tips. Other probes such as those utilizing laser energy delivery systems often provide pointed tips with curved configurations. with current probes, the surgeon has little control when pressing against a tough ligament. Now as the surgeon cuts through one portion of the ligament, the probe slips out of position. The surgeon must reapproximate the probe and cut again, an inefficient process. Unless the surgeon is able to stop pressure at exactly the right time, the probe may slip and cut an adjacent structure. Because the surgeon must repeatedly reapproximate and cut the ligament, the surgeon has difficulty in cleanly ablating the ligament or tendon. Thus, there are certain procedures that surgeons still prefer to perform in an open setting which is conventionally termed an "open" procedure. Unfortunately, this often results in large scars, long convalescence, and even more irritation of an already irritated joint.

What is needed is a probe that can simultaneously direct the tendon to the energy source (e.g., RF) and apply RF to cleanly and smoothly ablate the tendon or ligament. The advantage is that some procedures that have been considered too awkward or difficult to perform by arthroscopy can now be performed more effectively using arthroscopic devices.

Moreover, conventional and more complex surgical probes and lasers are less suitable for critical and precise shaping and sculpting of body tissues such as articular cartilage, ligaments and tendons. Target tissues subject to ablation and removal have many different configurations and structures. These medical device probes and lasers have further disadvantages of being configured for simple ablation without regard to the contour and structure of the target tissue. By universally applying RF energy to the site, non-target tissue may be affected by collateral thermal effects.

For these reasons, it would be desirable for an apparatus and method to selectively cut and ablate body tissue during a medical procedure such as arthroscopic surgery. The apparatus and method should be configured and used for effective cutting, ablation and vaporization of target tissue while giving the surgeon a precise and controlled surface for scraping tissue from bone or sculpting tissue within the surgical field for appropriate treatment and therapy. Such apparatus and methods should also be applicable in a wide variety of medical procedures on a wide range of different bodily tissues. The apparatus should also be simple and less expensive to manufacture while being compatible with conventional systems and procedures.

SUMMARY OF THE INVENTION

One embodiment of the invention is based on a surgical apparatus, comprising: an energy application tip including: a length of shaft; and an active electrode having a curved current density edge with at least one convex surface.

Another embodiment of the invention is based on a method of surgically treating a mammal in need thereof, comprising: providing a surgical instrument including a length of shaft and an active electrode having a curved current density edge with at least one convex surface; and ablating a tissue surface with said surgical instrument.

Another embodiment of the invention is based on an electrosurgical system for directing thermal energy to tissue is disclosed which has a power supply and a probe. The probe is coupled to the power supply by a cabling means and has a handle and a shaft including a distal end and a proximal end. The shaft has at least one lumen for an active electrode electrically coupled to the power supply, the active electrode being positioned on the distal end of the probe, the active electrode having an energy application surface; and a return electrode electrically coupled to the power supply.

These, and other, goals and embodiments of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

DESCRIPTION OF SPECIFIC EMBODIMENTS

Figure 1:
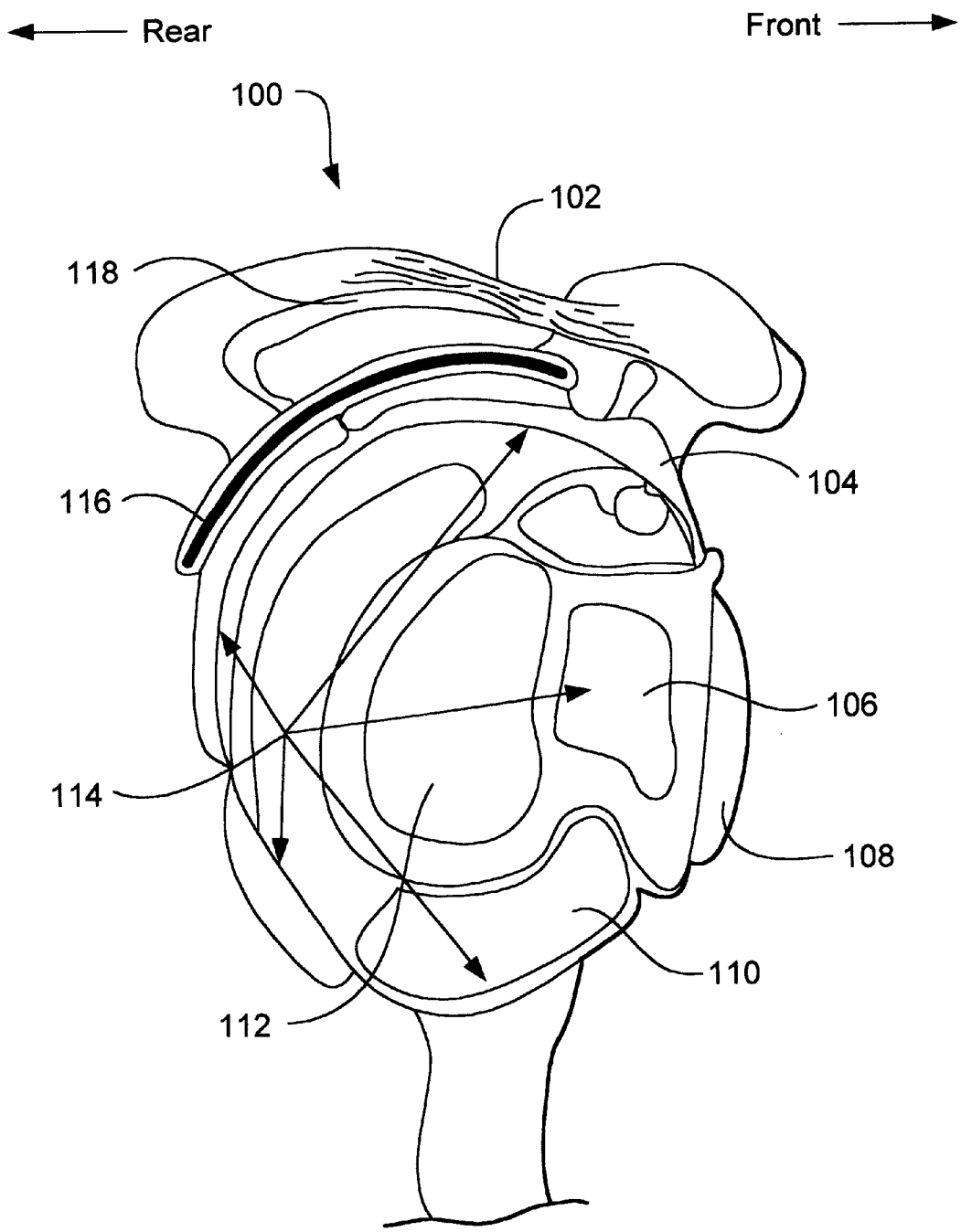
FIG. 1 is a lateral view of internal structures within the glenohumeral joint.

The invention arose out of an observation that, during an arthroscopy procedure, the surgeon could not access and cut cleanly the coracoacromial (CA) ligament shown in FIG. 1. This procedure is done in conjunction with a subacromial decompression, which makes a painful shoulder easier to move. If the cutting probe slips, the joint capsule could be damaged and even punctured, which would exacerbate an already painful joint. Thus, a concave rounded tip was designed which would center and position ligaments and could even be used to lift the ligament away from adjacent structures and avoid harm thereto.

This new style of tip has the advantage of being able to mechanically "gather" or constrain ligaments, tendons and other tissue into its center. This reduces the natural tendency of current cutting probes to slide off ligaments and tendons. This helps save time in that the surgeon is not repeatedly trying to center or approximate the probe tip on the target tissue.

FIG. 1 shows a lateral (side) view of a glenohumeral joint 100 and in particular the Coracoacromial ligament 102, the Superior glenohumeral ligament 104, the middle glenohumeral ligament 106, the Subscapularis Tendon 108 (joined to capsule), the Inferior Glenoheumeral ligament 110, the Glenoid "cup" with cartilage 112, the Joint Capsule 114, and the Bursa 116. The Joint Capsule 114 is comprised of 3 glenohumeral ligaments and surrounding capsule. The Bursa 116 lubricates and acts like a shock absorber, and is usually removed when an SA decompression is performed. The area 118 is the area at which impingement usually occurs.

Figure 2:
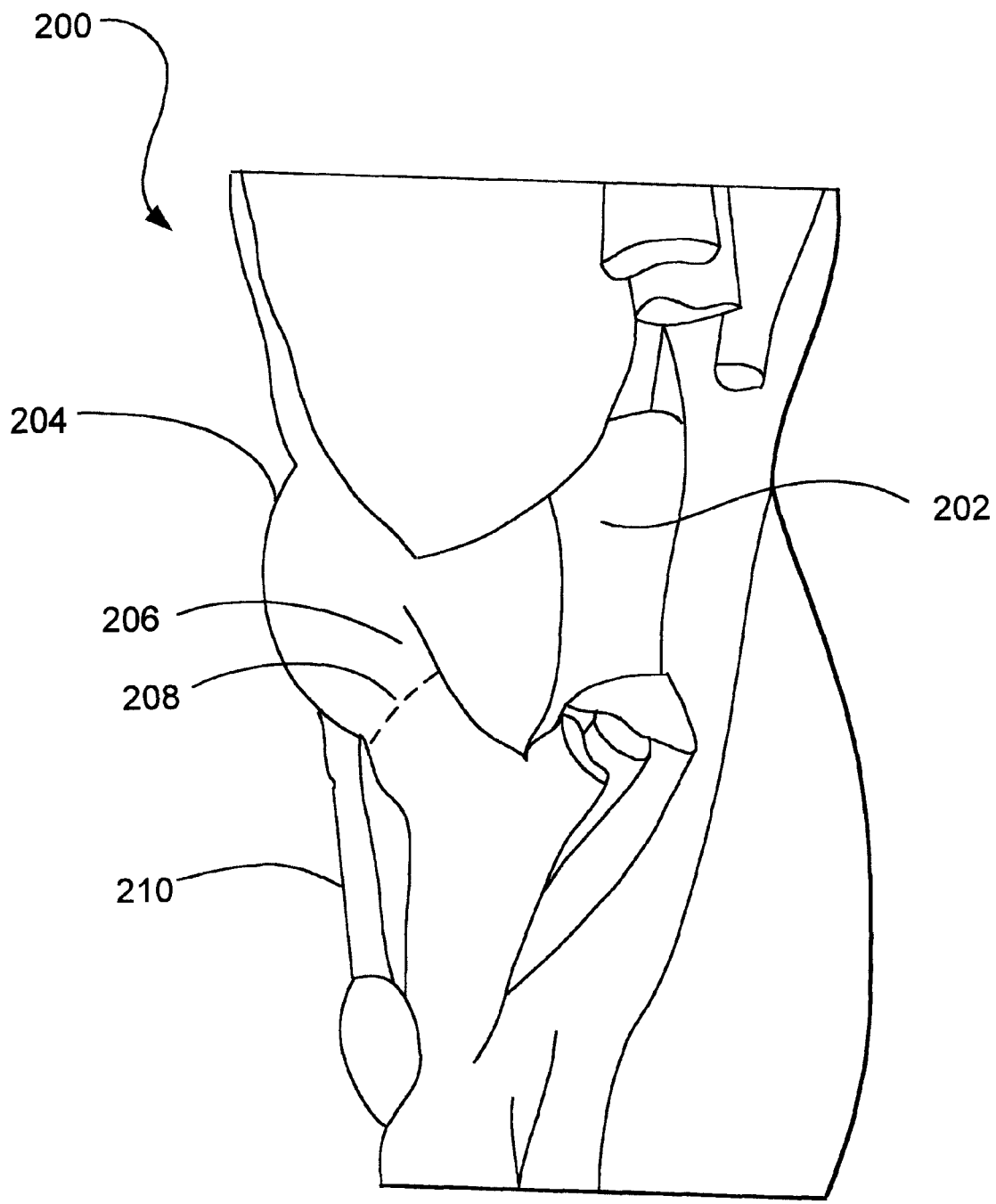
FIG. 2 is a medial side view of the knee joint.

FIG. 2 shows a medial (side) view of a patellofemoral or knee joint 200, and in particular the Medial Collateral Ligament 202, the patella 204, the Medial Lateral Retinaculum 206, an incision line 208 for lateral release and the Patellar Ligament 210.

Figure 3:
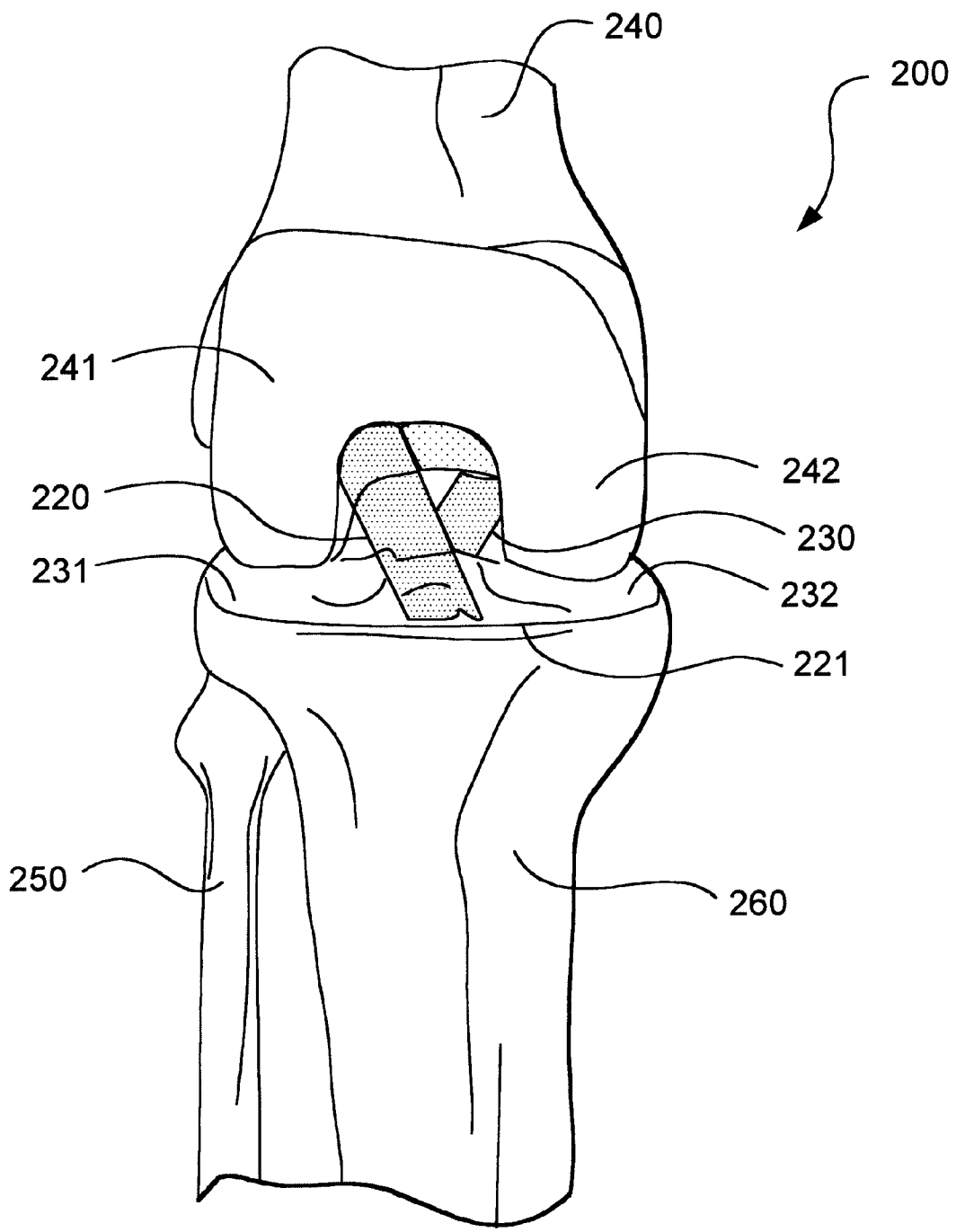
FIG. 3 is an anterior view of the knee joint with the patella removed.

FIG. 3 illustrates an anterior view of the knee joint 200 with the patella removed. The bones comprising the knee joint 200 are the femur 240, the fibula 250 and the tibia 260. The joint is connected by ligaments, in particular, the anterior cruciate ligament 220 and the posterior cruciate ligament 230. As the knee is flexed, the lateral condyle of the femur 241 and the medial condyle of the femur 242 articulate and pivot on the meniscal surfaces of the tibia, in particular the lateral meniscus 231 and the medial meniscus 232, respectively. The meniscal surface comprises articular meniscal cartilage which acts as the shock absorber for the knee.

While coracoacromial surgery was the inspiration for this invention, use of this concave probe is not limited to a particular ligament or tendon, or even to those soft tissues. The concave cutting probe is adapted to cut all types of tendons, ligaments and soft tissues more effectively than blunt or rounded tip probes. As another example whose anatomy is shown in FIG. 2, the lateral retinaculum 206 sometimes must be severed in some types of patellar dislocation or malignment, when the patella is not properly tracking in the trochlear notch. Severing the lateral retinaculum is called lateral retinacular release. With this concave-tip probe, the surgeon is able to position the ligament and sever it cleanly.

The probe of the invention may also be used in the knee joint during a notchplasty procedure for anterior cruciate ligament repair. The probe configuration of the invention, in particular the energy application tip configuration is used to remove and scrape the condylar surfaces of the femur to increase the interchondylar notch to free the anterior cruciate ligament from impingement. The anterior cruciate ligament may also be cut at point 221 and removed using the probe and a patellar tendon graft may be performed.

Figure 4:
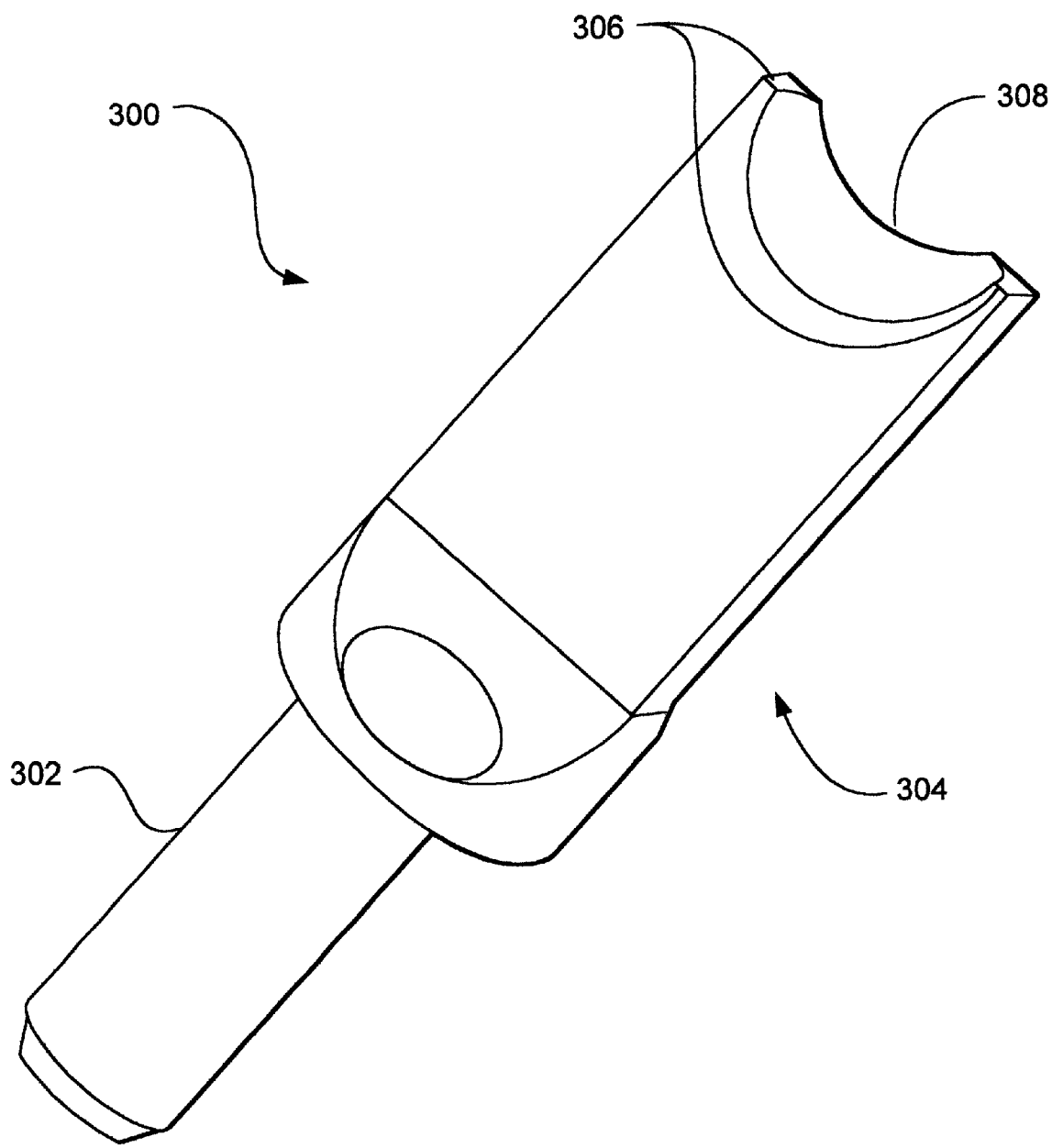
FIG. 4 is a perspective view of a concave cutting tip of a RF probe.
Figure 5:
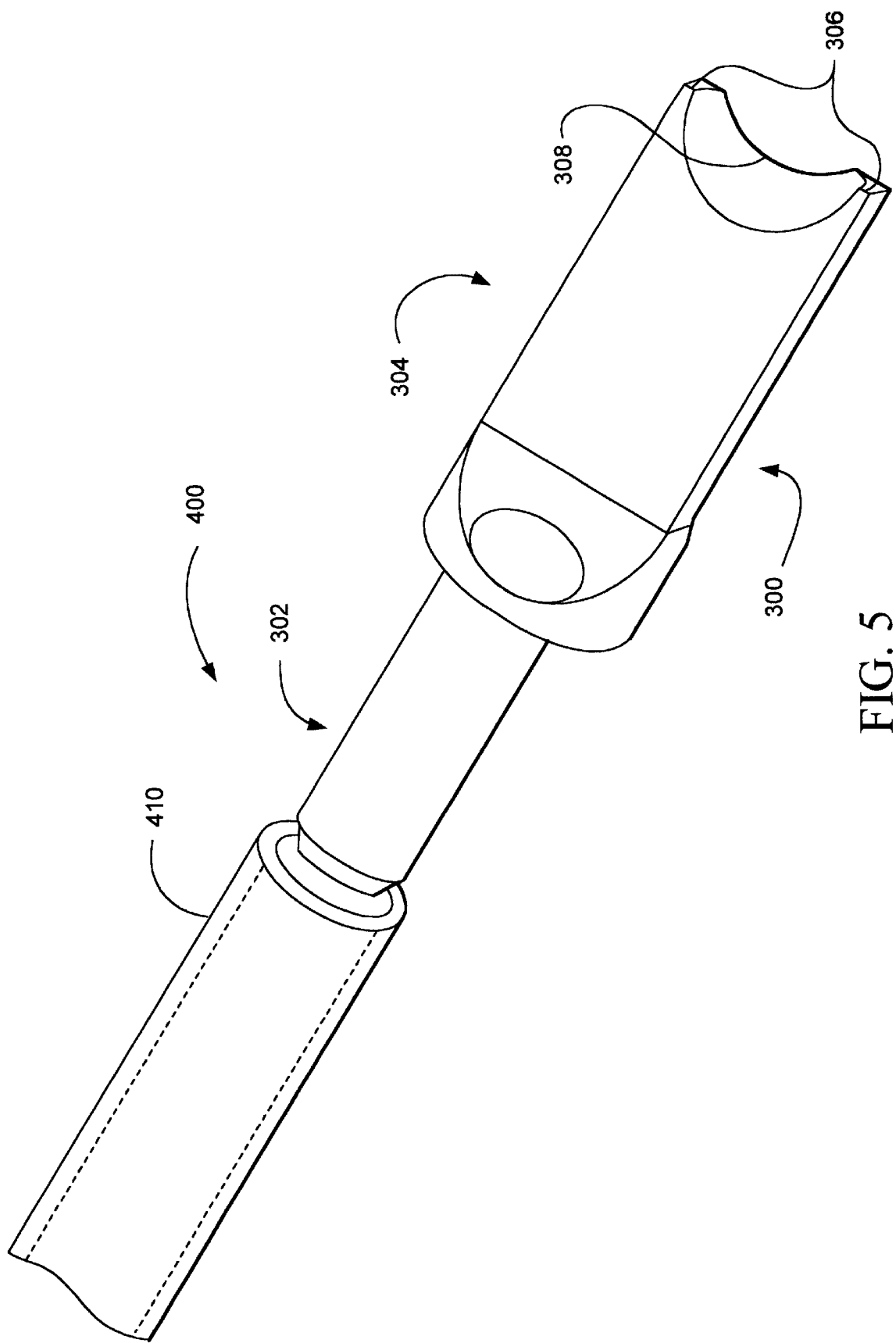
FIG. 5 is a perspective view of the concave cutting tip of FIG. 4 inserted into the shaft portion of the RF probe.

Turning now to the probe itself, FIG. 4 shows a concave edge 308 on a distal tip 304 of an RF probe head 300. This concave edge is designed to constrain tissue, tendons and ligaments. The concave curve has lateral edges 306 which are rounded, so that the probe does not "snag" on unwanted tissue as the surgeon maneuvers the probe into position. The cylindrical portion 302 of the distal tip 304 fits inside probe sheath 410, as shown in FIG. 5. The distal tip may have a variety of configurations, as shown in FIGS. 4–11. FIG. 5 shows probe 400 having a concave edge with less prominently rounded lateral edges. FIGS. 5–7 show a distal tip which is angled with respect to the sheath 410. This embodiment offers the advantage of helping the surgeon get around corners and ablate in narrow or confined spaces.

Figure 6A:
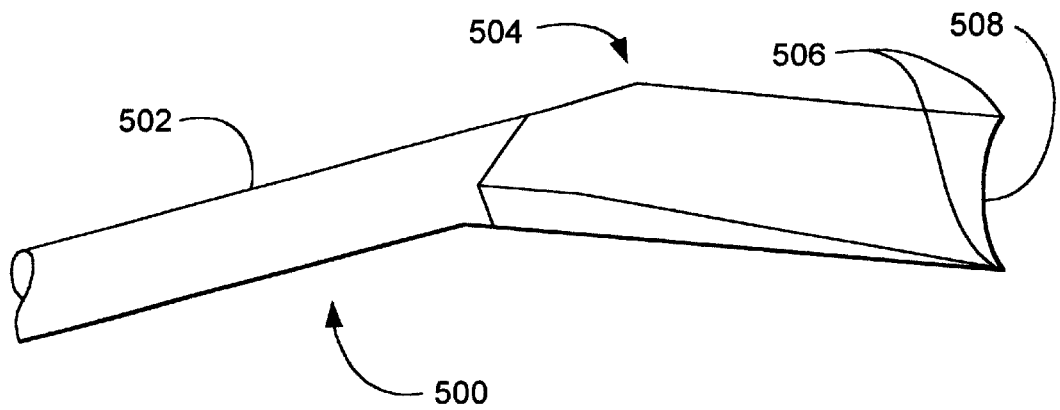
FIGS. 6A–B are side views of the concave cutting tip of the RF probe of FIG. 4.
Figure 6B:
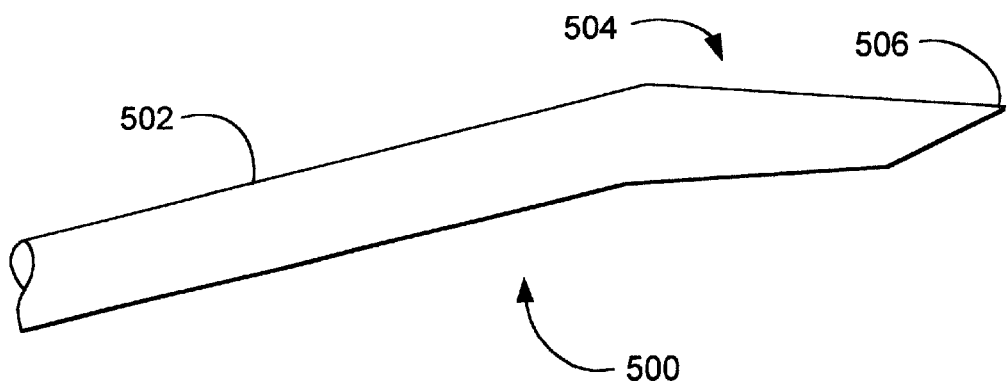
Figure 7:
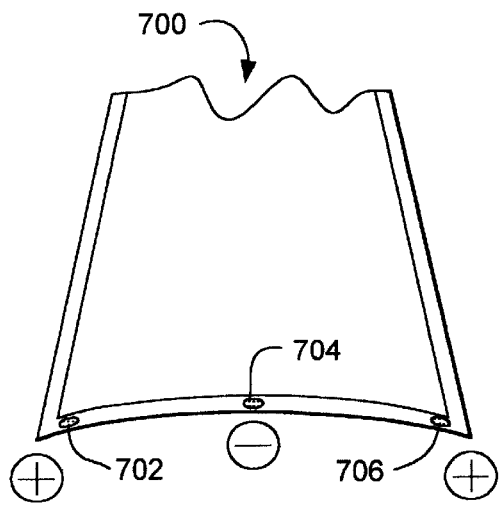
FIGS. 7–11 show different monopolar and bipolar arrangements of the electrodes on the concave cutting tip.

FIG. 6A shows an angled probe 500 consisting of a cylindrical portion 502 with a distal tip 504 having a concave edge 508 and lateral edges 506. FIG. 6B shows a side view of angled probe 500.

Figure 6C:
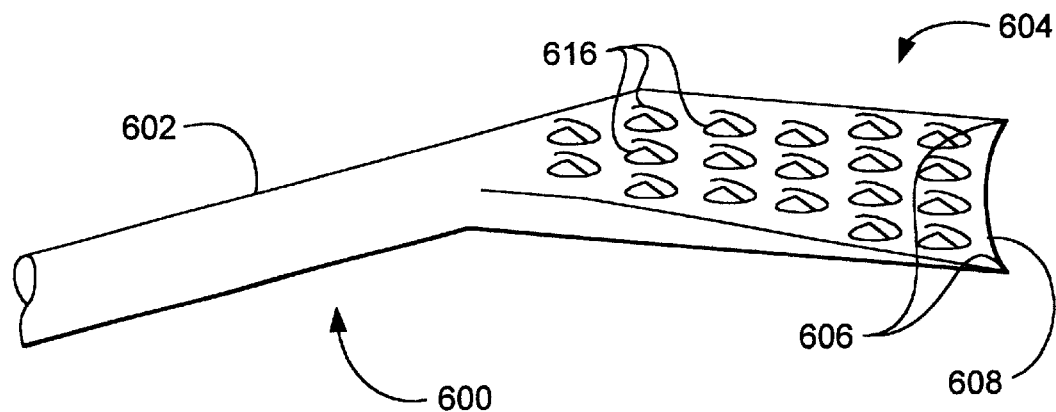
FIG. 6C is an alternative embodiment of the concave cutting tip of the RF probe.

FIG. 6C shows an angled probe 600 with a specialized surface (not heated) which imparts a third function to the probe, namely scraping tissue. Probe 600 is comprised of a cylindrical portion 602, and a distal tip 604 which has a concave edge 608 and lateral edges 606. The surface of the flat portion of distal tip 604 contains rasps 616 which can be used for scraping tissue.

Figure 8:
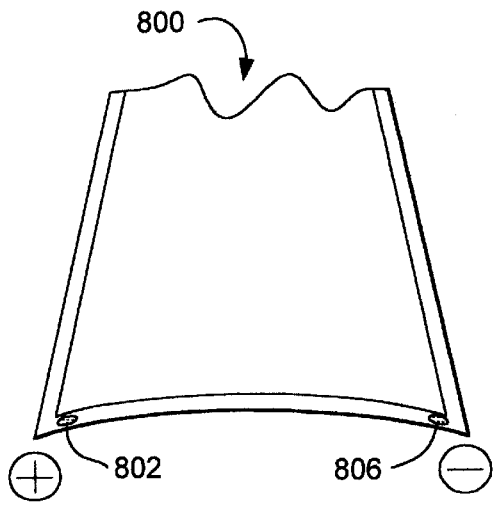

For cutting tissue, the distal tip has a first electrode and a second electrode located on lateral edges 606. The first and second electrodes can be operated in bipolar or monopolar mode. Bipolar is preferred and examples of "Taser" type electrodes are shown in FIGS. 7 and 8.

Figure 9:
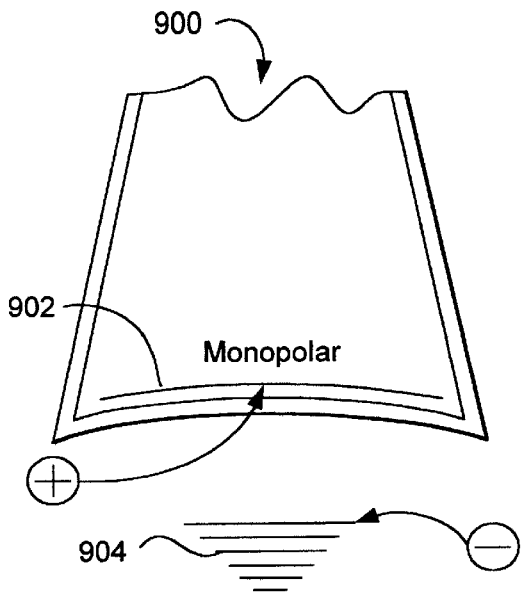
Figure 10:
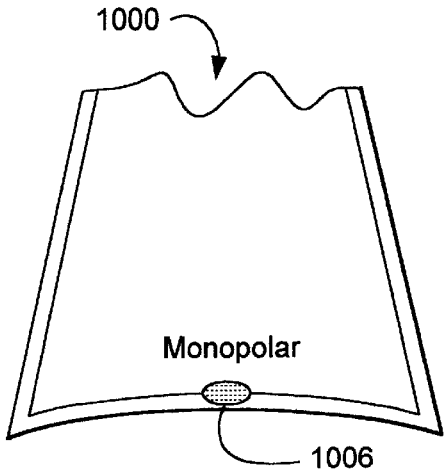
Figure 11:
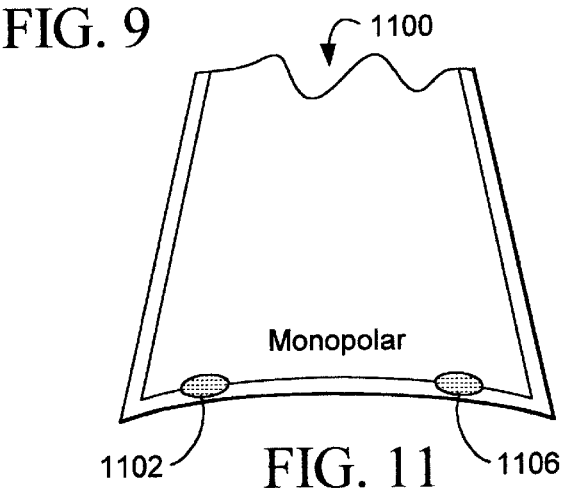

FIG. 7 shows a distal tip 700 having a three-pole, bipolar arrangement where, in addition to two side positive electrodes 702 and 706, there is a central negative electrode 704. FIG. 8 shows a distal tip 800 wherein two electrodes 802 and 806 are positioned in two small sites on the lateral edges of the concave curve. In this particular embodiment, electrode 802 is positive and electrode 806 is negative FIGS. 9–11 show exemplary monopolar arrangements. In FIG. 9, a single monopolar positive electrode 902 occupies a wide portion of the concave curve of distal tip 900. A return path 904 is provided and is attached to the patient's body to complete the circuit. In FIG. 10, there is one small active electrode 1006 located centrally on distal tip 1000. In FIG. 11 there are two active electrodes 1102 and 1106 in lateral positions on distal tip 1100. Suffice it to say that quite a variation in electrode design is contemplated for this concave curve.

To maintain the appropriate temperature for cutting tissue, the distal tip of the probe may also be equipped with a thermocouple, but such a thermocouple is optional in the concave-tipped probe.

Figure 12A:
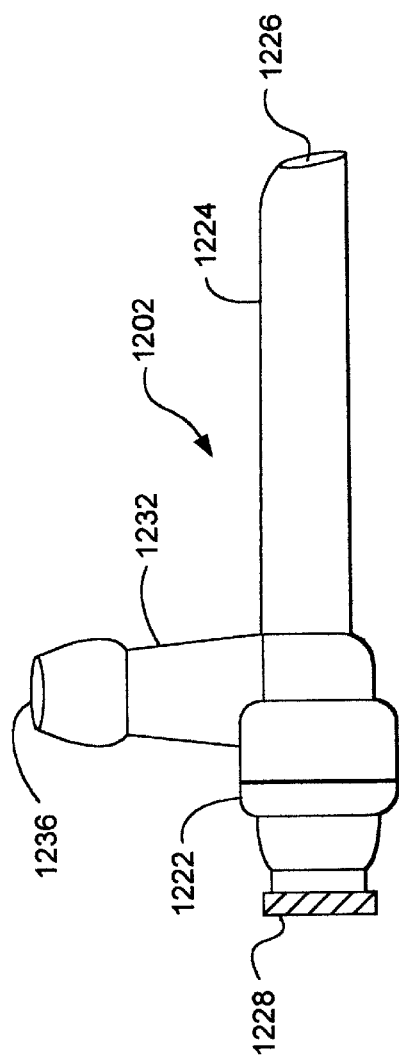
FIGS. 12A–C show an overview of a RF probe, operating cannula and a side, cross-sectional view of the shaft portion of the RF probe.
Figure 12B:
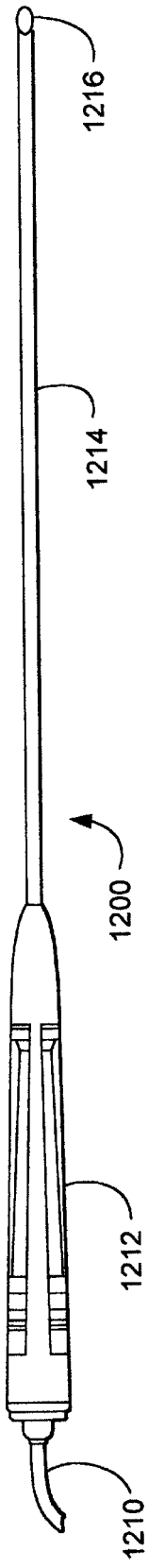

FIG. 12 illustrates a simplified view of the RF probe of the invention. FIG. 12A is an illustration of a conventional cannula utilized in one embodiment of the invention. Cannula 1202 consists of a guide 1224 with an opening 1226 at its distal end. Cannula 1202 is attached at its proximal end to introducer 1222. Instrument port 1228 is located at the proximal end for the introduction of the surgical probe. Cannula 1202 may also have an extension 1232 with a fluid port 1236. As illustrated in FIG. 12B, surgical instrument 1200 consists of a handle 1212 to which is attached a power cord 1210, a probe shaft 1214 and a probe tip 1216. During introduction into the body, a blunt insert or obturator (not shown) is inserted through instrument port 1228. Cannula 1202 is inserted into the surgical site on the patient functioning as a trocar. Surgical instrument 1200 is then inserted into cannula 1202 through instrument portal 1228 so that the tip 1216 protrudes from the opening 1226 in cannula 1202.

Figure 12C:
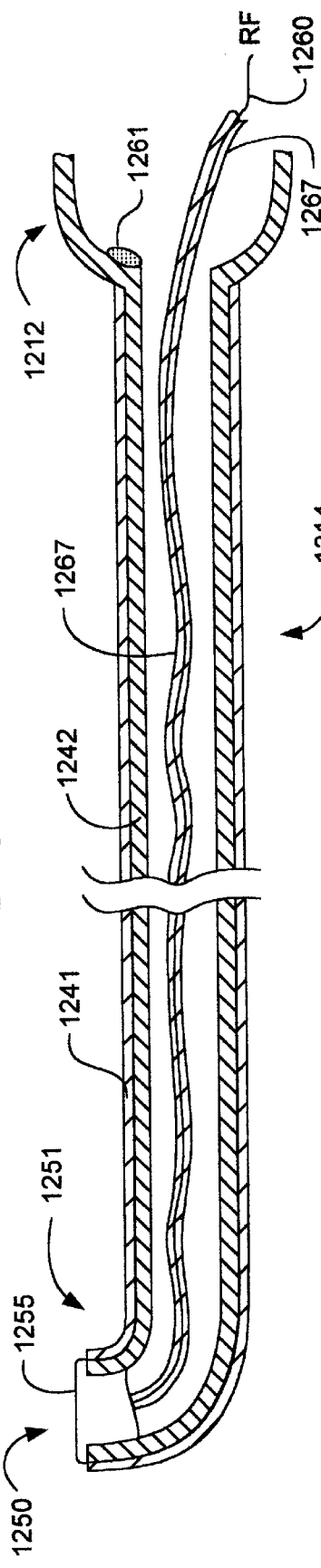

FIG. 12C illustrates a side, cross-section of the probe shaft 1214. Probe handle 1212 is connected to shaft tubing 1242. Shaft tubing insulator 1241 covers the shaft tubing. The shaft tubing insulator 1241 may be any biocompatible material such as Teflon or any other suitable material such as nylon shrink tubing. Power wire 1260 is connected to a power supply (not shown) in the proximal portion of the probe and probe handle 1212. Power insulator 1267 covers and insulates power wire 1260. The power insulator 1267 material is preferably a tubing such as Teflon or polyimide but may also include any other insulator material which would be known by a person skilled in the art such as a coating. Power wire 1260 connects the power supply to an active electrode (not shown) on the distal energy application tip 1250. The power wire may be stainless steel, titanium, tungsten, copper or any other compatible and suitable conductor. A return wire 1261 connects a return electrode (not shown in FIG. 12) to the power supply. The energy application tip 1250 has an energy application surface 1255. The energy application surface 1255 is configured to have a variety of configurations such as concave, convex or concavo-convex for the delivery of thermal energy to the soft tissue site. Probe shaft tubing 1242 may also have a bent portion 1251 which may be configured for easier access to narrow or confined joint spaces.

Figures 13A, 13B:
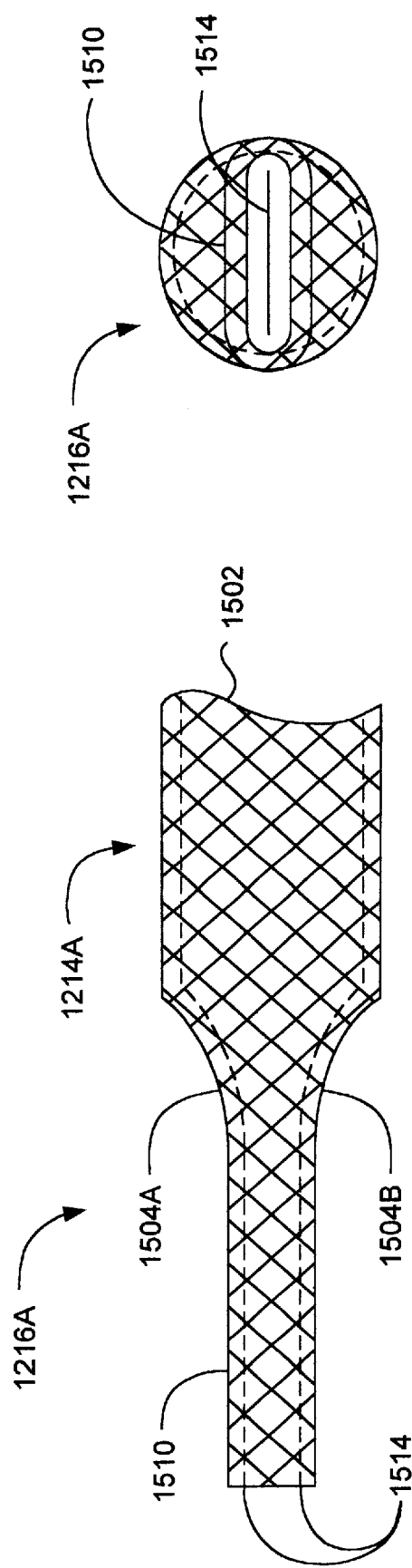
FIGS. 13A–B illustrates an alternate embodiment of a probe with cutting tip.

FIGS. 13A–B show an enlarged view of one embodiment of the tip 1510 of an electrosurgical instrument wherein two opposing arcuate segments 1504A and 1504B are compressed to form a probe tip 1216A at the distal end of probe 1214A. In such an embodiment, swagging is used to compress the tip of the probe. Swagging forms a chisel 1514 that can be used in the surgical instrument of FIGS. 12 and 13 for RF ablation of tissue. Grinding applications can be added to the tip to provide for mechanical tissue ablation in addition to energy ablation. The core 1502 of probe 1214A can be either hollow or solid. This particular embodiment is illustrated as having an annular probe. Probe 1214A is coated in an insulating material which terminates prior to the tip 1510, leaving chisel 1514 exposed. The surgical probe illustrated in FIGS. 13A–B provides various improvements over the prior art in allowing for precise hemostatic cutting and ablation of soft tissue in one convenient instrument which can be described as a chisel. The malleable probe tips can be configured as straight, angled or curved, for example, which provides for optimal access to specific anatomy and pathology. Unique tip designs improve tactile feedback for optimal control and access, and provide for improved tissue visualization with greatly reduced bubbling or charring.

Figure 14A:
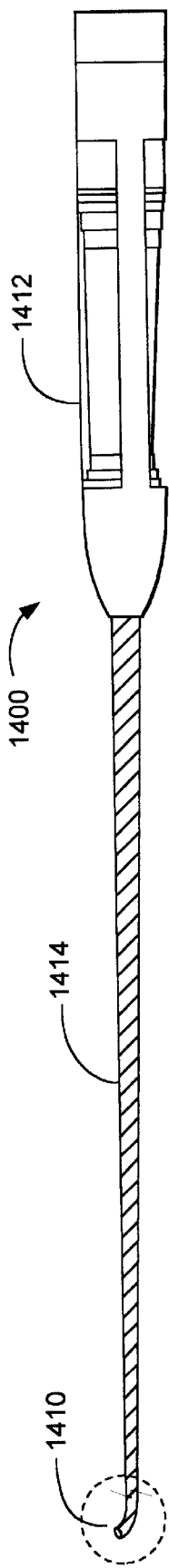
FIG. 14A is a simplified, side view of the probe according to the invention.
Figure 14B:
FIGS. 14B–14F show alternative tip configurations of the probe.
Figure 14C:
Figure 14D:
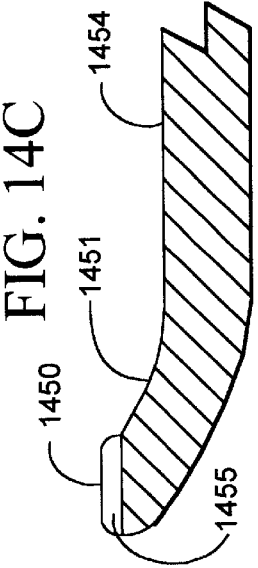
Figure 14E:
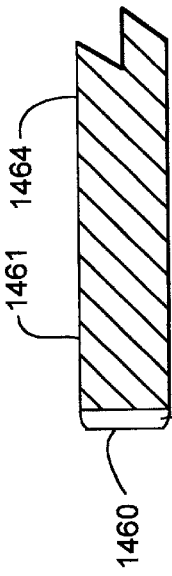
Figure 14F:
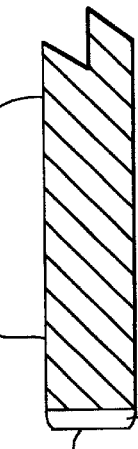

Another embodiment of surgical probe of the invention is illustrated in FIGS. 14A–F. FIG. 14A illustrates a simplified side view of the surgical probe for the delivery of thermal energy to a tissue site. FIGS. 14B–F show various alternative embodiments of the energy application tip. The configuration of the probe shaft allows the surgeon to have better access and more selective control while in the operating environment. For example, FIG. 14D is particularly suitable for use in an arthroscopic acromioplasty wherein the coracoacromial ligament is cut and associated tendons are removed. The right angle of the energy application tip allows the surgeon to scrape target tissue from the underside of the acromion. The various other configurations and geometries of the energy application tip as shown in FIGS. 14B–14F allow the surgeon to operate in a variety of arthroscopic procedures to access various joint geometries within the body. The probe may also be malleable to allow the surgeon to adjust the distal tip for an individual and procedure.

Figure 15A:
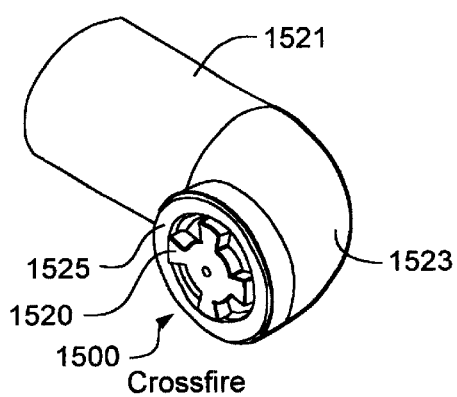
FIGS. 15A–C are isometric, top and cross-sectional views, respectively, showing one embodiment of an active electrode and an energy application tip of the probe according to the invention.
Figure 15B:
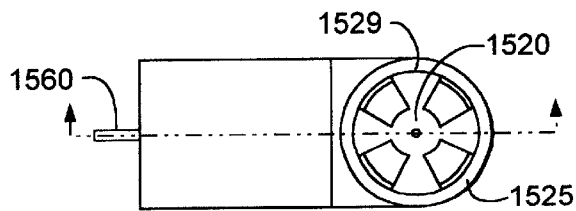
Figure 15C:
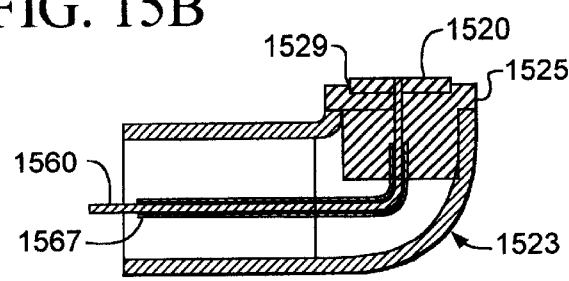

FIGS. 15A–15C illustrate one embodiment of the distal energy application tip of the probe according to the invention. The energy application surface comprises an active electrode 1520 in the form of a "cross" or "crossfire" for the delivery of electrical energy to a tissue site during a surgical procedure. The electrical characteristics of this cross-shape design and configuration of the active electrode 1520 condenses and concentrates the electrical current density at defined current density edges 1529 along cross-shape on the distal tip. The return electrode 1523 is also located near the distal energy application tip such that a unipolar arrangement for RF energy delivery is described. An insulating collar 1525 separates active electrode 1520 from return electrode 1523.

Turning to FIG. 15C, power wire 1560 delivers energy from the power source to the active electrode 1520. Power insulator 1567 insulates the power wire inside the probe and between the shaft tubing and electrodes. Insulating collar 1525 insulates the active electrode 1520 from the return electrode 1523 which may be formed from a portion of the shaft tubing or a separate electrode on the distal tip. Alternatively, a separate return electrode structure may be used which is separate from the distal energy application tip. The current travels between the active electrode and the return electrode through the irrigation solution or through the tissue.

For example, it will be appreciated by one skilled in the art that in an alternating current system, the generated and delivered high frequency RF energy (greater than 300 kHz) will alternate between the active electrode 1520 and the return electrode 1523. By using a larger surface area return electrode in proportion to the active electrode, the RF energy is diffuse in the area of the return electrode. When the energy is applied to the distal energy application tip, heat is generated at the sharp edges 1529 of active electrode 1520 activating the entire electrode surface while heat is minimized at the return electrode 1523 through diffusion. Because electrical current is condensed and concentrated on a smaller area, heat is generated at a directed and desired area such as the target tissue in contact with the energy application tip. This allows the surgeon to cut and ablate the target tissue in a more efficient manner when the tissue causes an increase in impedance between the two electrodes. The cross configuration and edges 1529 also provides a specific mechanical surface for a physical scraping function of the active electrode. The tissue and standard irrigation in the surgical joint complete the circuit between the two electrodes and the tissue is mechanically and thermally cut and ablated allowing the surgeon to vaporize the target tissue such as when removing a soft cartilage tissue from bone.

Thus, the distal energy application tip of the invention may be further described as "unipolar" or "sesquipolar" whereby one electrode has a different electrical potential than the other electrode. In a true bipolar system, each electrode would have equal potentials and equal effects when electrical energy is applied to the active electrodes. In the invention, the active electrode generates heat by condensing the RF energy at the sharp edges causing cutting, ablation and vaporization while the return electrode generates little heat. It will also be appreciated that due to the high frequency current, these distal energy application tips and active electrode designs may be used in conventional monopolar surgical systems where the return electrode is located on the patient's body.

Figure 15D:
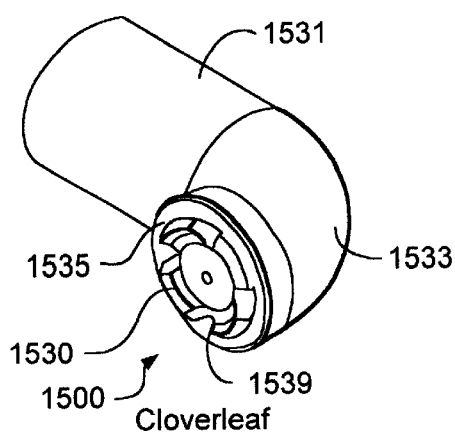
FIGS. 15D–F are isometric, top and cross-sectional views, respectively, showing an alternate embodiment of the active electrode.
Figure 15E:
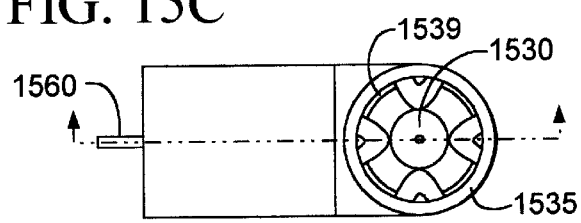
Figure 15F:
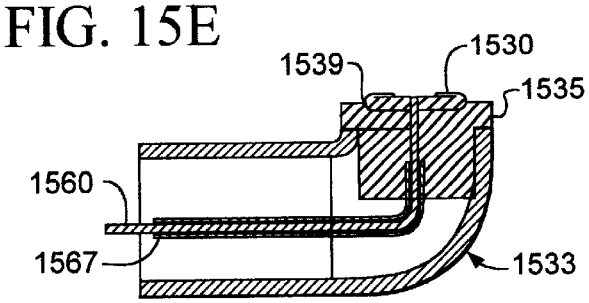

FIGS. 15D–F illustrate another embodiment of the distal energy application tip 1500 of the invention wherein the active electrode 1530 is constructed in a "cloverleaf" configuration. As described in FIG. 15A, the RF energy is condensed and directed through current density edges 1539 towards the target tissue. Active electrode 1530 has the mechanical advantage of a greater scraping ability by providing a sharp current density edge 1539. Power wire 1560 is covered with power insulator 1567 and delivers energy to the active electrode 1530. It will be appreciated that all current density edges will have the same current potential whereby the potential for an ablation and vaporization effect is uniform at all tissue contact points.

Figure 15G:
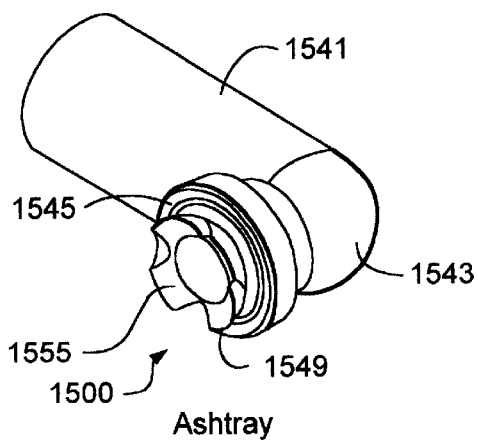
FIGS. 15G–I are isometric, top and cross-sectional views, respectively, showing an alternate embodiment of the active electrode and distal tip of the probe.
Figure 15H:
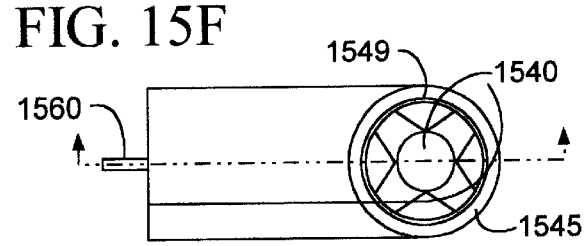
Figure 15I:
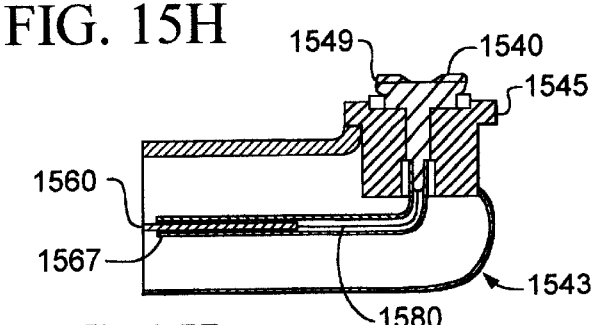

FIGS. 15G–I illustrate another embodiment of the distal energy application tip 1500 of the invention wherein the active electrode 1540 is an "ashtray" configuration. As described in FIG. 15A, the RF energy is condensed and directed through current density edges 1549 towards the target tissue. Active electrode 1540 has a further mechanical advantage of a greater scraping ability by providing a sharp current density edge 1549 while having a thermal energy effect at the current density edges 1549. Power wire 1560 is covered with power insulator 1567 and delivers energy to the active electrode 1540. It will be appreciated that all current density edges will have the same current potential whereby the potential for an ablation and vaporization effect is uniform at all tissue contact points. As the RF power is delivered to the active electrode, the target tissue in contact with the surface of the current density edges 1549 is uniformly cut and ablated for removal from the joint. FIG. 15I also shows the power wire 1560 alternatively coupled to the distal tip 1540 by means of an intermediate couple wire 1580.

It will also be appreciated that the active electrode can be brazed, crimped soldered, welded or mechanically attached by means of a spring clip to the power wire. One alternative attachment means includes providing an active electrode with a hole. When the electrode is heated, the hole expands and the power wire is inserted into the hole. As the electrode tip cools, the diameter of the hole will decrease thereby effectively crimping the electrode tip to the power wire. Further, the active electrode may consist of titanium, tungsten and their alloys or stainless steel and the power wire may consist of stainless steel in a variety of tensile strengths, titanium, copper or any suitable alloys thereof. The active electrode tip may also be machined, stamped, cast into shape or metal injection molded to form the desired configuration with current density edges.

Figure 16A:
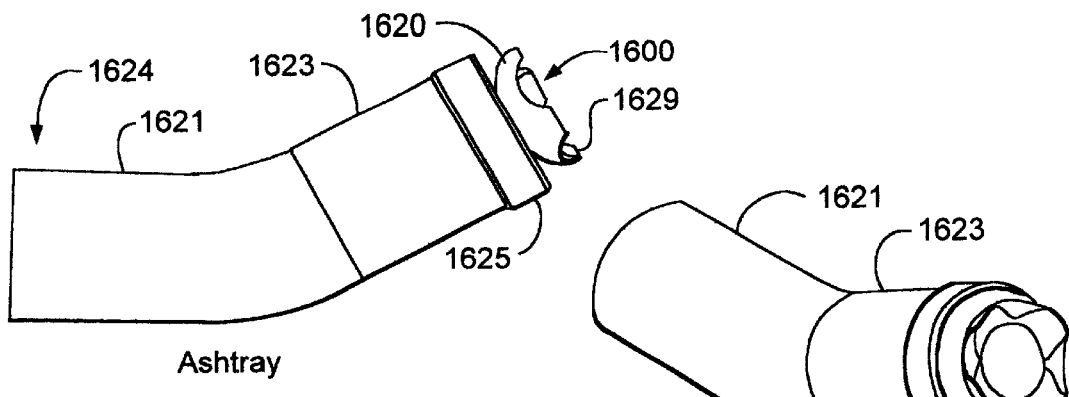
FIGS. 16A–F are side and isometric, perspective views of different embodiments of the probe according to the invention.
Figure 16B:
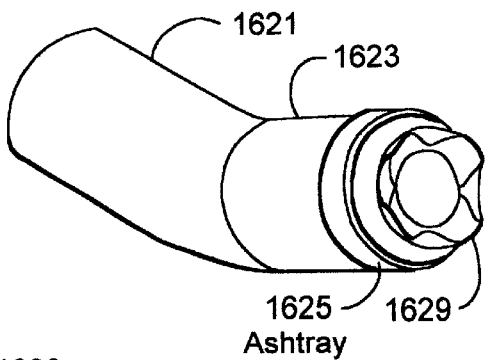

FIG. 16A–B show side and perspective views of ashtray electrode configured for sculpting soft tissue attached to bone or any other soft tissue within the body. The distal energy application tip is arcuate such that the shaft tubing is bent between 0 and 90 degrees. The shaft 1624 is preferably 30 degrees to provide an angle for sculpting the soft tissue by ablation. In this embodiment, the return electrode 1623 is formed from the distal portion of the shaft tubing and electrically connected to the power supply to act as the return in a unipolar configuration.

As shown in FIG. 16A, the current density edge 1629 has cutouts or gaps whereby the RF energy is focused primarily on the external edges of the active electrode thereby heating up specific areas of target tissue adjacent to the probe. As the power level of the RF energy increases, the target tissue is cut and ablated in a consistent pattern to vaporize the tissue along the current density edge 1629 as the surgeon manipulates the probe within the surgical field.

Figure 16C:
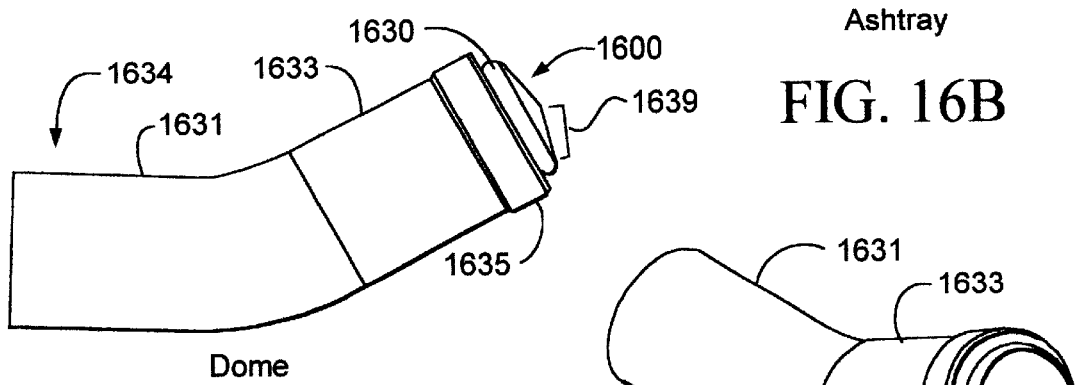
Figure 16D:
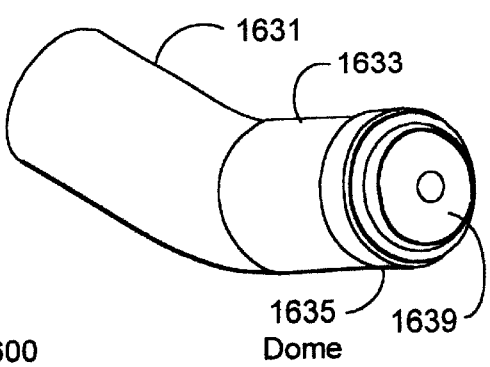

In FIGS. 16C–D, the active electrode is shown in an alternative embodiment having a dome structure with a convex surface for ablation and vaporization. Active electrode 1630 has a simple base with a dome defining a broad surface current density edge. As the RF power is applied to the active electrode, the target tissue is sculpted in a smooth and consistent ablation. Surgical procedures using a smoothing ablation and vaporization include meniscal repair and capsulotomy where extra cartilage and ligament material can irritate the joint if it is not cut out and removed by ablation and vaporization.

Figure 16E:
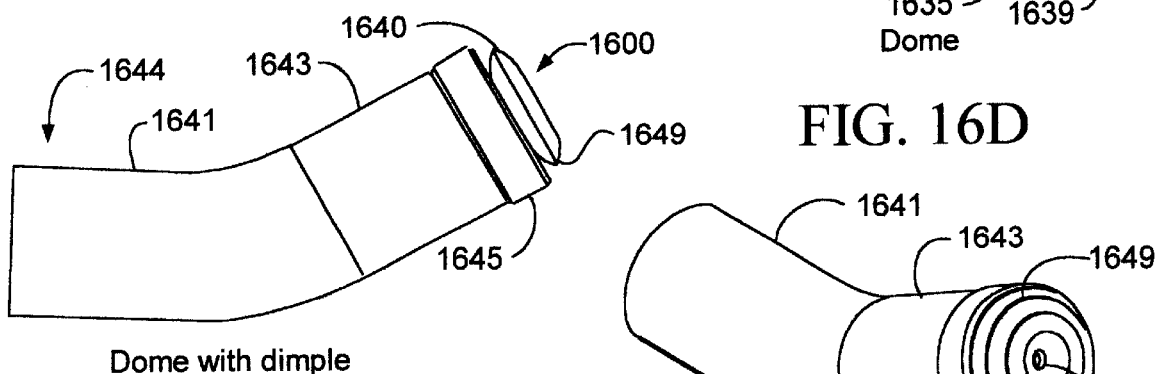
Figure 16F:
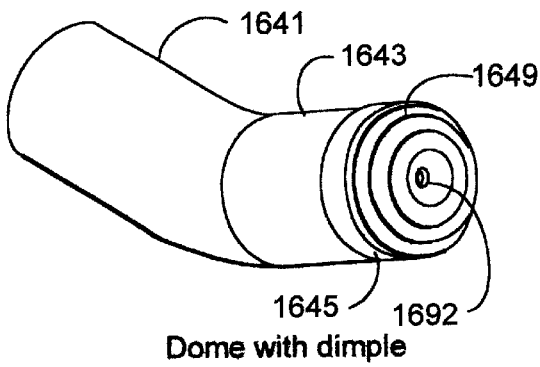

FIGS. 16E–F illustrate an alternative embodiment wherein the dome of FIGS. 16C–D has a dimple within the convex dome structure. As the vaporization occurs, constant bubble streams with small bubbles resulting from cellular destruction and dessication obscure the operating field and arthroscope where the surgeon views the arthoscopic procedure. The dimple allows the bubbles to collect and form a larger bubble which is then released from the void defined by the dimple at an infrequent rate. This allows the surgeon to have an unobstructed view of the tip while still allowing the energy application tip 1600 to deliver RF energy to the active electrode so as to effect ablation. Current density edges 1649 provide for a condensation and concentration of RF energy along the edges of the active electrode 1640 to heat up the target tissue in contact with the edges thereby causing ablation and vaporization.

Figure 17A:
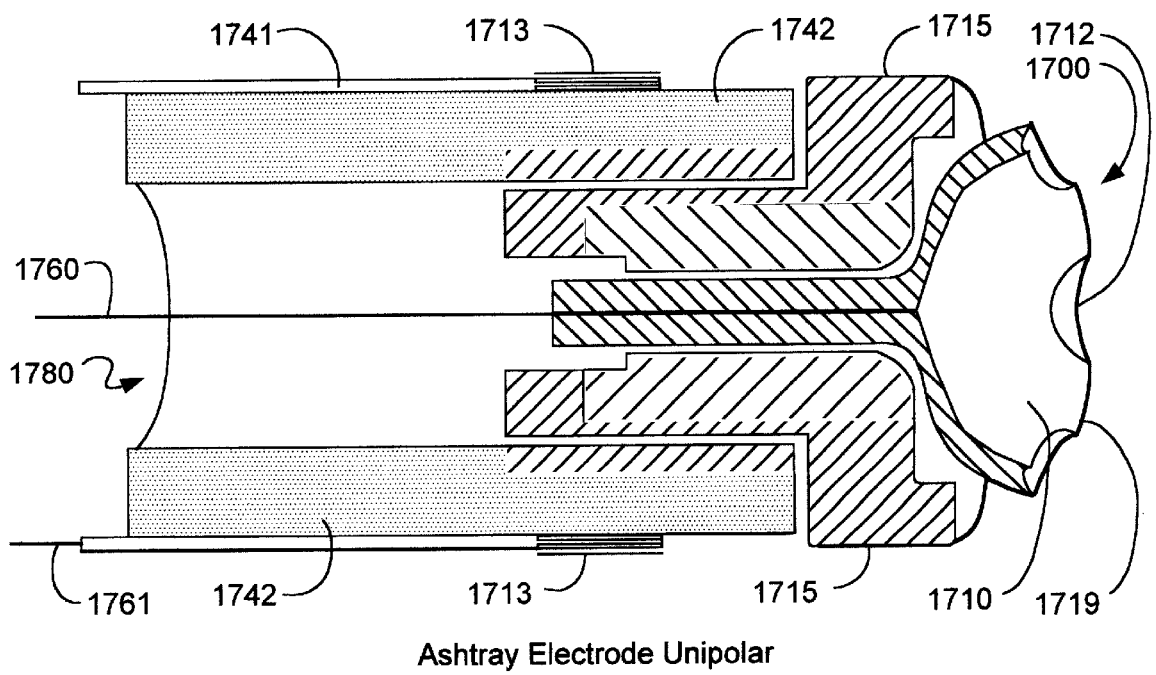
FIG. 17A is a cross-sectional view of one of the distal energy application tips and active electrode of the probe according to the invention.

Turning to FIG. 17A, the distal energy application tip 1700 is illustrated in a detailed cross-section. The active electrode 1710 is provided in an ashtray configuration. The current density edges 1719 are located on a distal portion of the active electrode. Gap portions 1712 allow the RF energy to be condensed and concentrated at the current density edges 1719. The active electrode 1710 is inserted into an insulating collar 1715 for attachment to the distal end of the shaft tubing 1742.

In a unipolar setting, the return electrode 1742 is located near the end of the distal tip of the shaft tubing 1742. Alternatively, the return electrode 1742 may be formed from a portion of the shaft tubing 1742 thereby allowing for a simpler construction. Shaft insulation 1741 insulates the shaft in conjunction with insulating collar 1715. Power wire 1760 delivers the RF energy to the active electrode from the power supply and is located within the shaft tubing lumen 1780. Return wire 1761 is coupled to return electrode 1713 to function as a return to the power supply.

Figure 17B:
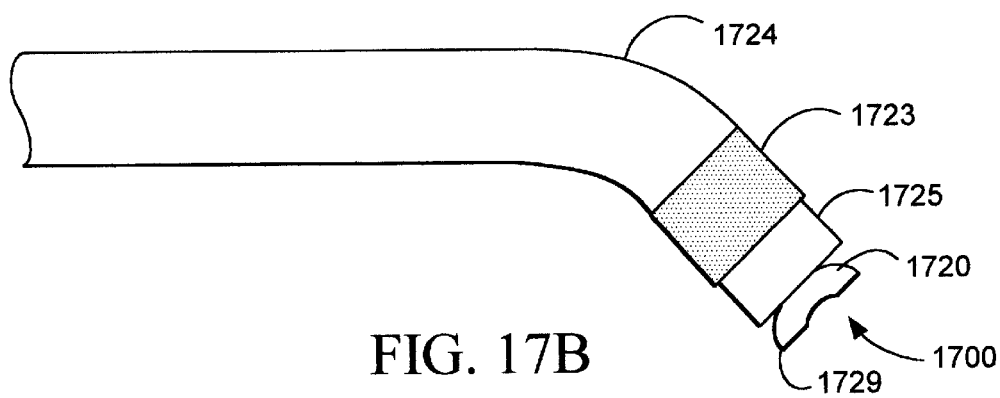
FIGS. 17B–C are side views of different embodiments of the probe.
Figure 17C:
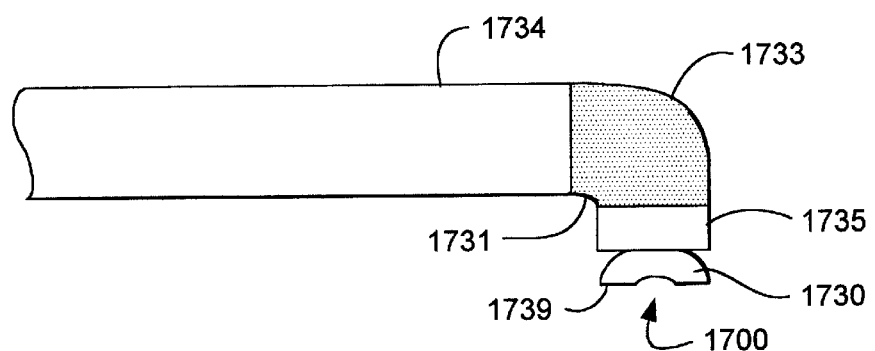

FIGS. 17B–C show alternative embodiments of the shaft with the ashtray active electrode. FIG. 17B illustrates the ashtray active electrode being configured for sculpting the target tissue wherein the distal end of the shaft 1724 is bent to a right angle. The active electrode 1720 with current density edges 1729 is located on the distal portion of shaft 1724. The return electrode 1723 is separated from active electrode 1720 by insulating collar 1725.

FIG. 17C illustrates the ashtray active electrode being configured for scraping target tissue from bone. The active electrode 1730 with current density edges 1739 is located on the distal portion of shaft 1734. The return electrode 1733 is separated from active electrode 1730 by insulating collar 1735.

Figure 18A:
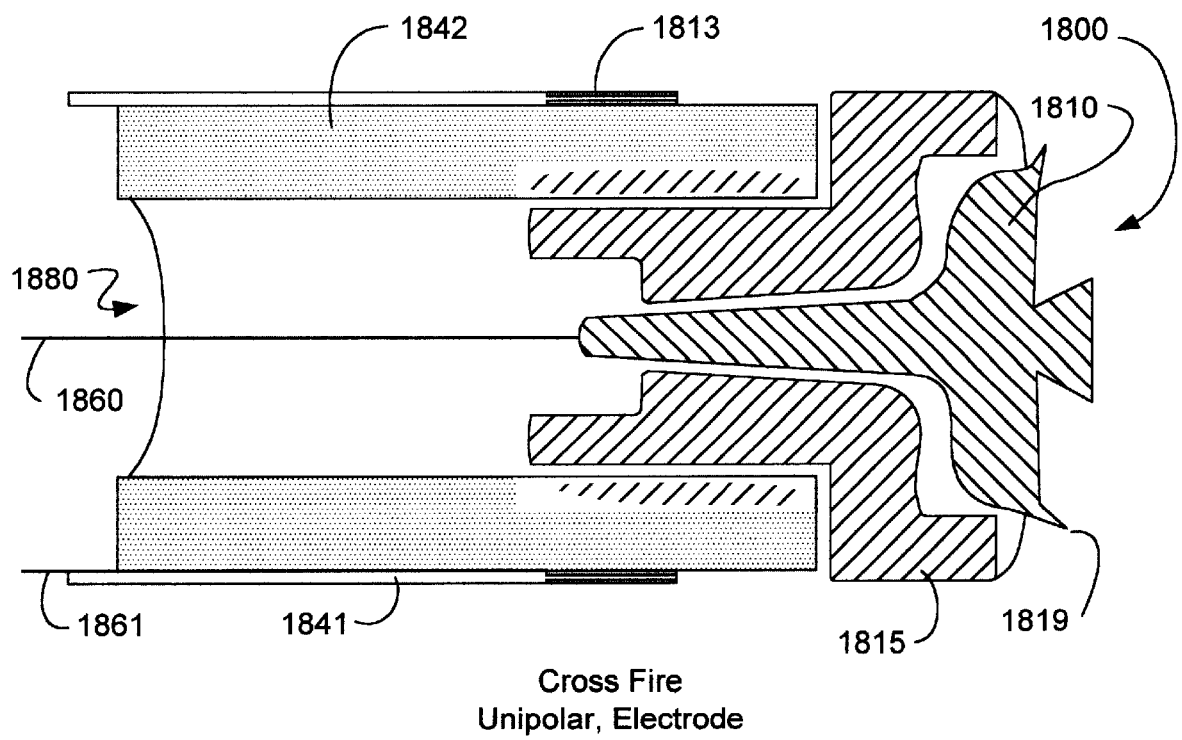
FIG. 18A is a cross-sectional view of an alternative embodiment of the distal energy application tip and active electrode of the probe according to the invention.
Figure 18B:
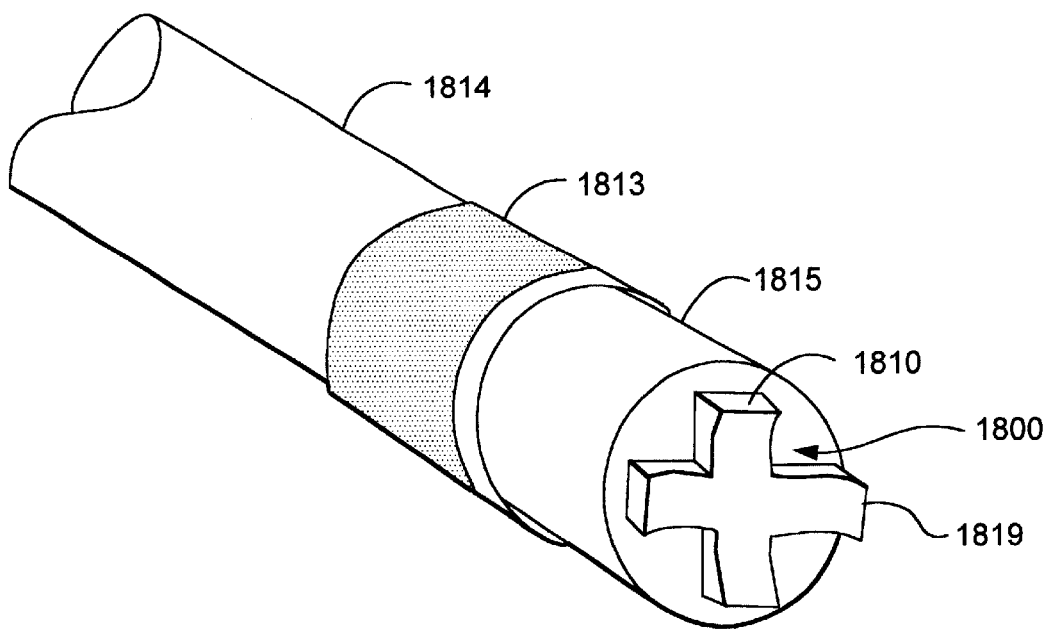
FIG. 18B is an isometric perspective view of the probe.

FIG. 18A–B shows a detailed cross-section and perspective view of the distal energy application tip 1800 with a cross-configured active electrode 1810. In an exemplary embodiment, the active electrode 1810 is insulated from return electrode 1813. The return electrode 1813 may also be formed from a portion of the shaft tubing 1842. Power wire 1860 located within the shaft tubing lumen 1880 delivers RF energy to the active electrode 1810. The current density edges 1819 provide a surface for the current to condense causing ablation and vaporization of the target tissue. Shaft insulation 1841 protects and insulates shaft tubing 1842.

Figure 19A:
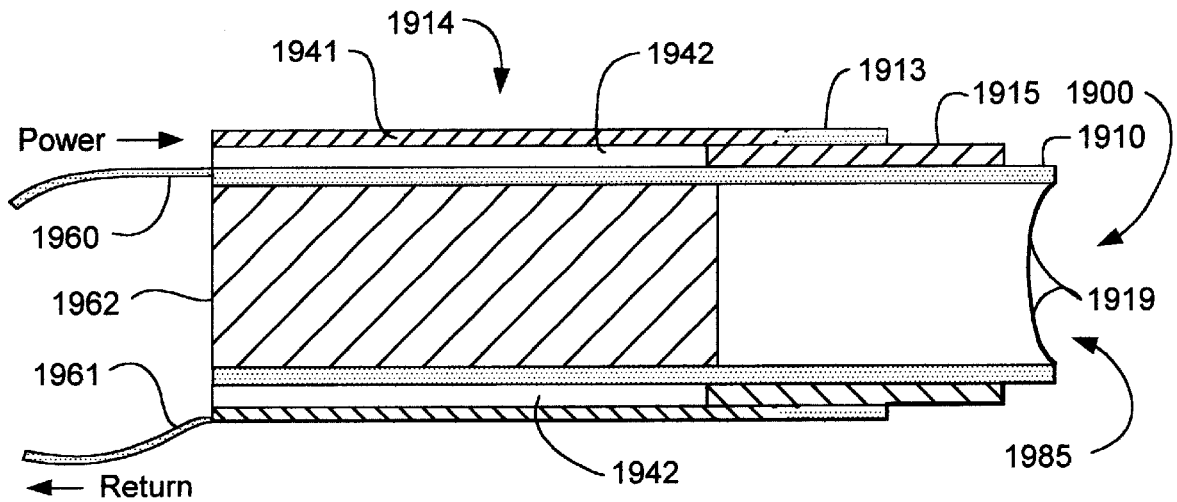
FIGS. 19A–B are side, cross-sectional views of an alternative embodiment of the distal energy application tip and active electrode of the probe according to the invention.
Figure 19B:
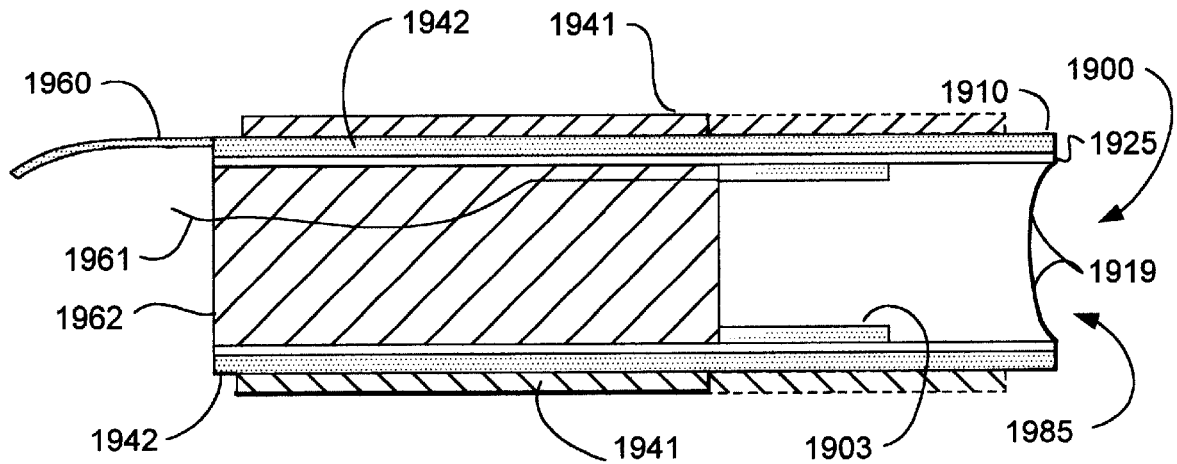

FIG. 19A–B illustrate another embodiment of the active electrode wherein the distal energy application tip 1900 is configured for grating. In this embodiment, active electrode 1910 is a ring electrode with a continuous current density edge 1919. In this configuration, the active electrode defines a lumen 1985 with insulator block 1962 forming the back wall portion of the lumen. Insulator collar 1915 insulates the active electrode 1910 from the return electrode 1913. Insulator collar 1915 is attached to the distal portion of shaft tubing 1942. The shaft 1914 is covered in shaft insulator 1941. In FIG. 19B, the return electrode 1903 is located within active electrode lumen 1985. In this configuration, a boiling chamber is created wherein any additional material that is grated and scraped into the lumen and not fully ablated or vaporized will increase the impedance between the active and return electrodes to cause further vaporization. As the ring electrode is placed against target tissue and RF energy is delivered through power wire 1960, ablation and vaporization occurs at the current density edge 1919.

Figure 20A:
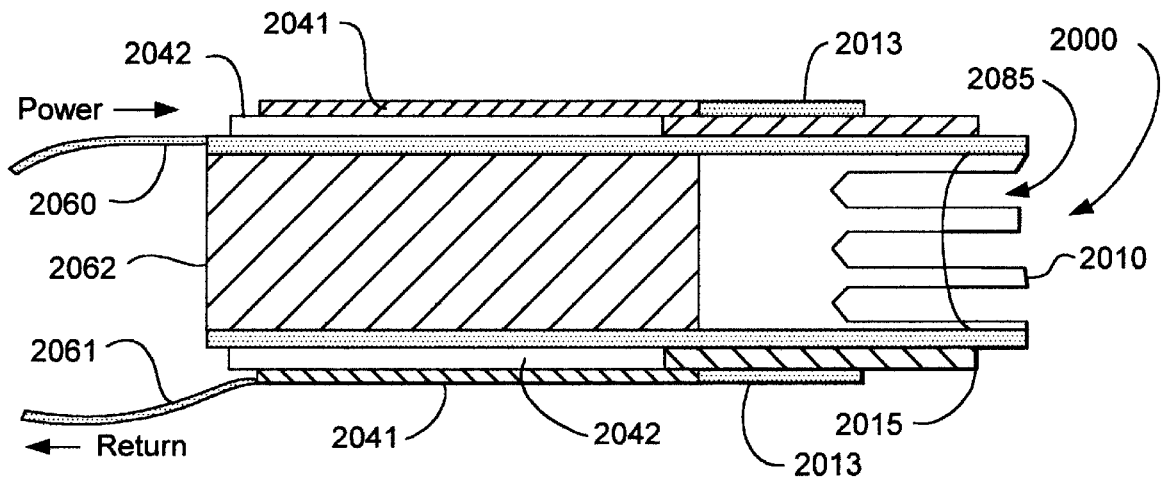
FIGS. 20A–B are side, cross-sectional and isometric perspective views, respectively, of the probe of the invention.
Figure 20B:
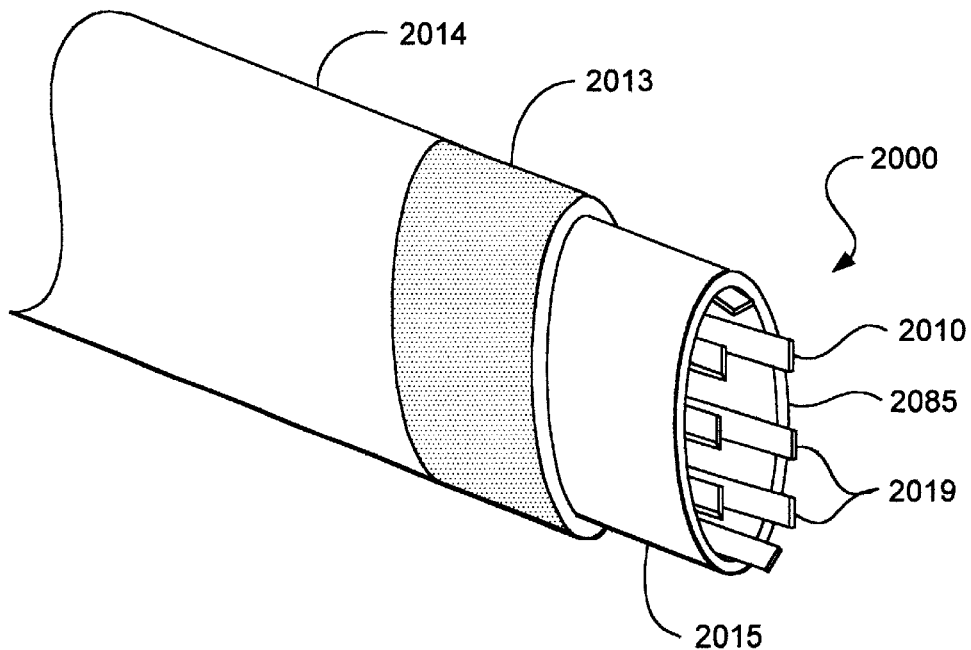

FIG. 20A–B illustrate an alternative embodiment of the distal energy application tip 2000 wherein the active electrode 2010 has a complex teeth structure for mechanical grating during ablation and vaporization. In this embodiment, the active electrode 2010 is formed from by machining or cutting curves or teeth into the ring electrode. In this configuration, the current density edges 2019 provide a tooth-like grater to mechanically scrape the target tissue. RF power is delivered by power wire 2060 through insulating block 2062. The active electrode 2010 is insulated from return electrode 2013 by insulating collar 2015. The insulating collar 2015 is located on the distal portion of shaft tubing 2042 which is insulated by shaft insulator 2041. Return wire 2061 is coupled to return electrode 2013 to function as a return to ground at the power supply. While shaft 2014 is shown as linear, it may be malleable or pre-bent to allow for appropriate access and control within the surgical environment.

EXAMPLE

Lateral retinacular release as mentioned above can be accomplished with the use of the concave-tipped RF probe as shown in FIG. 4. First, the knee joint is distended with a clear fluid, usually saline. Initial distention can be done using a large syringe full of saline which is injected into the joint space. Distention forces the bones of the joint apart creating room to introduce instrumentation without damaging the cartilage.

Once the instrumentation has been inserted into the joint space, the irrigation tubing and cannulas are positioned and hooked up to provide continual fluid exchange during the procedure. The most common systems are gravity flow or the use of an arthroscopic pump. By hanging bags of irrigation fluid on an IV pole and raising them 3–4 feet above the operative site, flow to the joint can be accomplished. Elevation of the supply bag is enough to create pressure to distend and irrigate the joint. The fluid enters the joint through the scope sheath and exits through a cannula placed in the superior lateral portal, or the reverse, through the cannula and out through the scope sheath. The setup is a matter of physician preference. The key to the proper function of either system is that the inflow volume must be larger than the outflow volume. This restriction in the outflow is what creates the back flow that distends the joint.

With an arthroscopic pump, the bags do not need to be raised on an IV pole. The factors controlling distention of the joint are controlled automatically by the pump. The pump monitors the fluid pressure in the joint space using a pressure sensing cannula and automatically increases or decreases fluid flow as needed to provide optimum viewing. As with the gravity flow system, fluid enters the joint cavity through the scope sheath or the cannula in the superior lateral portal. Such an arthroscopic procedure requires the creation of two to five portals (entry ways) into the joint capsule. To create a portal, the surgeon usually begins by making a small stab wound with a scalpel (e.g., No. 11 or 15 blade) at the site of the portal. Next, the wound is enlarged and extended with a trocar encased in a sleeve (cannula) through muscle tissue to the synovial membrane. The trocar is removed, leaving the cannula in place. Then, the surgeon uses a blunt obturator (to avoid damage to menisci and articular cartilage) to puncture through the synovium into the joint cavity. The obturator is removed and the cannula left in place. The cannula can be used to insert an arthroscope or for the inflow and outflow of water. If the surgeon elects to insert instruments percutaneously, the sleeve is removed. For lateral retinacular release, the surgeon frequently uses three portals, one for the arthroscope, one for the instrument and one for the drain. Additional portals may be created for the surgeon to access other areas of the knee (i.e., to tighten the medial retinaculum) during the procedure. Frequently, a superolateral (above and to the side of the patella) approach is used for the irrigation cannula. For the arthroscope and concave probe, anteromedial and anterolateral approaches often are chosen, because they are relatively safe (minimal potential tissue damage) and most surgeons have more experience with them. Once the arthroscope is viewed, the surgeon may use the concave-tipped probe (without power) to advance to the site of the lateral retinaculum. Having located the lateral retinaculum, the surgeon activates the RF probe and cuts entirely through the ligament.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

All publications and patent applications mentioned in this specification are herein incorporated by reference to the same extent as if each individual publication or patent application was specifically and individually indicated to be incorporated by reference.

While the invention has been described with respect to its preferred embodiments, it will be appreciated that other alternative embodiments may be included. For example, with respect to all of the explicitly disclosed embodiments, as well as all other embodiments of the invention, monopolar implementation may be achieved by replacing the return electrode on the probe with a separate return electrode, or alternatively, simply providing an additional electrode as a return electrode on the body of a patient electrically utilizing the return electrode on the probe. These and various other modifications can be made to the disclosed embodiment without departing from the subject of the invention.

What is claimed is:

1. A surgical apparatus, comprising:
   an energy application tip including:
      a length of shaft having an end; and
      an active electrode extending distally of the end of the shaft, the active electrode having a base formed by the end of the shaft and a substantially cylindrical wall extending distally of the base, the wall having a convex outer surface extending distally and radially outwardly to a substantially circular current-density concentrating edge forming a rim of the active electrode.

2. The surgical apparatus of claim 1, wherein said length of shaft includes a substantially linear section near the tip.

3. The surgical apparatus of claim 1, wherein said convex outer surface arcs distally and radially outwardly.

4. The surgical apparatus of claim 1, wherein said wall has an inner surface extending distally and radially outwardly to the substantially circular current-density concentrating edge.

5. The surgical apparatus of claim 1, wherein said active electrode defines an ashtray pattern.

6. The surgical apparatus of claim 1, wherein the wall is provided with a plurality of cutouts therein so that when electrical energy is supplied to the active electrode the electrical energy is focused on the rim of the active electrode.

7. The surgical apparatus of claim 6, wherein the plurality of cutouts are circumferentially spaced apart around the rim of the active electrode.

8. The surgical apparatus of claim 1, further comprising an insulating collar coupled to a distal end of said shaft.

9. The surgical apparatus of claim 8, wherein said length of shaft includes a return electrode that defines said distal end of said length of shaft.

10. The surgical apparatus of claim 9, further comprising a return wire coupled to said return electrode.

11. The surgical apparatus of claim 1, wherein said length of shaft includes a curved section having a substantially constant radius of curvature.

12. The surgical apparatus of claim 11, wherein said active electrode defines an ashtray pattern.

13. The surgical apparatus of claim 11, further comprising an insulating collar coupled to a distal end of said shaft.

14. The surgical apparatus of claim 13, wherein said length of shaft includes a return electrode that defines said distal end of said length of shaft.

15. The surgical apparatus of claim 14, further comprising a return wire coupled to said return electrode.

16. The surgical apparatus of claim 1, wherein said length of shaft includes an arcuate section.

17. The surgical apparatus of claim 16, wherein said active electrode defines an ashtray pattern.

18. The surgical apparatus of claim 16, further comprising an insulating collar coupled to a distal end of said shaft.

19. The surgical apparatus of claim 18, wherein said length of shaft includes a return electrode that defines said distal end of said length of shaft.

20. The surgical apparatus of claim 19, further comprising a return wire coupled to said return electrode.

21. The surgical apparatus of claim 1, wherein said length of shaft includes a curved section having a right angle.

22. The surgical apparatus of claim 21, wherein said active electrode defines an ashtray pattern.

23. The surgical apparatus of claim 21, wherein said substantially circular current-density concentrating edge defines a dome with dimple pattern.

24. The surgical apparatus of claim 21, further comprising an insulating collar coupled to a distal end of said shaft.

25. The surgical apparatus of claim 24, wherein said length of shaft includes a return electrode that defines said distal end of said length of shaft.

26. The surgical apparatus of claim 25, further comprising a return wire coupled to said return electrode.

27. The surgical apparatus of claim 1, wherein said length of shaft is a length of shaft tubing and wherein said active electrode is adjacent an inner surface of said length of shaft tubing.

28. The surgical apparatus of claim 27, further comprising a return electrode adjacent an outer surface of said length of shaft tubing.

29. A surgical apparatus for ablating tissue, comprising:
   a energy application tip including:
      a length of shaft having an end; and
      an active electrode extending distally of the end of the shaft, the active electrode having a substantially planar base and a substantially cylindrical wall extending distally of the base, the wall tapering at it extends distally to a substantially circular current-density concentrating edge for forming a rim of the active electrode to scrape tissue when electrical energy is supplied to the active electrode.

30. The surgical apparatus of claim 29, wherein said length of shaft includes a substantially linear section.

31. The surgical apparatus of claim 29, wherein said length of shaft includes a curved section having a substantially constant radius of curvature.

32. The surgical apparatus of claim 29, wherein said length of shaft includes a curved section having an arcuate section.

33. The surgical apparatus of claim 29, wherein said length of shaft includes a curved section having a right angle.

34. The surgical apparatus of claim 29, wherein the wall is provided with a plurality of cutouts therein so that when electrical energy is supplied to the active electrode the electrical energy is focused on the rim of the active electrode.

35. The surgical apparatus of claim 34, wherein the active electrode defines an ashtray pattern.

36. The surgical apparatus of claim 34, wherein the active electrode defines a cloverleaf pattern.

37. A surgical apparatus for treating tissue in a body of a mammal comprising an elongate member having proximal and distal extremities and an active electrode mounted on the distal extremity of the elongate member, the active electrode being substantially cup-shaped and having an arcuately-extending edge around at least a portion thereof, the arcuately-extending edge serving as a current-density concentrating edge for ablating and sculpting the tissue when electrical energy is supplied to the active electrode and being provided with a plurality of cutouts therein for focusing the electrical energy on the arcuately-extending edge.

38. The surgical apparatus of claim 37 wherein the plurality of cutouts are circumferentially spaced apart around the edge.

39. The surgical apparatus of claim 38 wherein the plurality of cutouts are four in number and are spaced apart at 90° intervals.

40. The surgical apparatus of claim 38 wherein the active electrode defines an ashtray pattern.

41. The surgical apparatus of claim 38 wherein the active electrode defines a cloverleaf pattern.

42. The surgical apparatus of claim 37 further comprising an electrical lead extending from the proximal extremity to the distal extremity of the elongate member and secured to the active electrode for permitting electrical energy to be supplied to the active electrode.

43. The surgical apparatus of claim 37 further comprising a return electrode carried by the distal extremity of the elongate member and spaced from the active electrode.

44. The surgical apparatus of claim 37 wherein the elongate member has a substantially linear section.

45. The surgical apparatus of claim 37 wherein the elongate member has an arcuate section.

46. The surgical apparatus of claim 45 wherein the arcuate section has a substantially constant radius of curvature.

47. The surgical apparatus of claim 45 wherein the arcuate section has a right angle.

* * * * *

UNITED STATES PATENT AND TRADEMARK OFFICE
CERTIFICATE OF CORRECTION

PATENT NO. : 6,461,357 B1                                              Page 1 of 1
DATED       : October 8, 2002
INVENTOR(S) : Hugh R. Sharkey et al.

It is certified that error appears in the above-identified patent and that said Letters Patent is hereby corrected as shown below:

Title page,
Item [75], Inventors, replace "John A. Ashley" with -- John E. Ashley --.
Item [56], References Cited, FOREIGN PATENT DOCUMENTS, insert
-- GB 2,160,102 A  12/1985 --.

Column 1,
Line 8, replace "6,135,989" with -- 6,135,999 --.
Line 44, replace "with" with -- With --.

Column 9,
Lines 14 and 16, replace "return electrode 1742" with -- return electrode 1713 --.
Line 28, replace "to a right angle" with -- at an angle --.
Line 35, after "of shaft 1734." insert -- Shaft 1734 is bent at a right angle. --.

Column 12,
Line 53, replace "a energy" with -- an energy --.

Signed and Sealed this

Eleventh Day of November, 2003

JAMES E. ROGAN
*Director of the United States Patent and Trademark Office*